United States Patent [19]  [11] 3,948,988
de Rooij  [45] Apr. 6, 1976

[54] CYCLIC PROCESS FOR PREPARING AND WORKING UP A HYDROXYLAMMONIUM SALT SOLUTION

[75] Inventor: Abraham H. de Rooij, Geleen, Netherlands

[73] Assignee: Stamicarbon, B.V., Geleen, Netherlands

[22] Filed: Apr. 1, 1975

[21] Appl. No.: 564,085

Related U.S. Application Data

[63] Continuation-in-part of Ser. Nos. 422,711, Dec. 7, 1973, Ser. No. 422,713, Dec. 7, 1973, Ser. No. 114,172, Feb. 10, 1971, abandoned, and Ser. No. 114,171, Feb. 10, 1971, abandoned.

[52] U.S. Cl. ............................................. 260/566 A
[51] Int. Cl.² ...................................... C07C 131/04
[58] Field of Search ............................... 260/566 A

[56] References Cited
UNITED STATES PATENTS
3,429,920  11/1964  de Rooij ........................... 260/566 A Primary Examiner—Gerald A. Schwartz
Attorney, Agent, or Firm—Cushman, Darby & Cushman

[57] ABSTRACT

An improved cyclic process for producing cyclohexanone oxime is provided wherein the circulating reaction medium is subjected to a heat treatment of at least 40°C in the presence of nitrous gases as it circulates between the oxime synthesis zone and the hydroxylamine synthesis zone. The residual cyclohexanone oxime is hydrolyzed to cyclohexanone in said heat treatment in the presence of nitrous gases. The reaction medium is then stripped of cyclohexanone prior to recirculating to the hydroxylamine synthesis zone. In another embodiment of the invention the recirculating reaction mixture is heated to at least 50°C in the presence of nitrous acid as the mixture circulates between the oxime synthesis zone and the hydroxylamine synthesis zone, thus reducing the amount of residual cyclohexanone oxime and cyclohexanone to an insignificant amount.

2 Claims, 3 Drawing Figures

CYCLIC PROCESS FOR PREPARING AND WORKING UP A HYDROXYLAMMONIUM SALT SOLUTION

CROSS-REFERENCE TO RELATED APPLICATIONS

This is a continuation-in-part of my earlier applications: (a) Ser. No. 422,711 filed Dec. 7, 1973, and its parent application Ser. No. 114,172 filed Feb. 10, 1971, now abandoned, and (b) Ser. No. 422,713 filed Dec. 7, 1973, and its parent application Ser. No. 114,171 filed Feb. 10, 1971, now abandoned.

BACKGROUND OF THE INVENTION

The present invention relates to an improved cyclic process for preparing a hydroxylammonium salt solution and converting a ketone to an oxime with the hydroxyl amine or hydroxylammonium salt. The invention further relates in particular to an improved process for the preparation of cyclohexanone oxime from cyclohexanone.

The cyclic process for the preparation of oximes from hydroxylamine or a hydroxylammonium salt is carried out in an acidic, buffered, aqueous reaction medium containing buffer acids such as phosphoric acid, bisulfate or buffer salts derived from these acid and mixtures thereof. The reaction medium is circulated between a hydroxylammonium salt synthesis zone, where nitrate ions, which have been added to the reaction medium, are catalytically reduced with molecular $H_2$ to hydroxylamine, and an oximation zone where a ketone is added to react with the hydroxylammonium salt to produce an oxime. The nitrate ions consumed in the hydroxylammonium synthesis zone are added to the circulating reaction medium just before the reaction medium is introduced into the hydroxylammonium salt synthesis zone. The nitrate ions are generally added in the form of nitric acid of approximately 60 weight percent.

The nitrate ions in the hydroxylamine synthesis zone are first converted into hydroxylamine which in turn reacts with the available buffer acid in the reaction medium, forming the corresponding hydroxylammonium salt. The resulting solution obtained, containing hydroxylammonium salt, is withdrawn from the hydroxylamine synthesis zone and circulated to the oximation zone, where the hydroxylammonium salt, together with a ketone, which is also fed to the oximation zone, forms the corresponding oxime, with liberation of acid. The oxime is removed from the oxime synthesis zone. The reaction medium withdrawn from the oxidation zone contains small amounts of oxime and ketone. This aqueous reaction medium is then returned to the hydroxylamine synthesis zone.

The chemical reactions taking place during the successive steps of the process for the preparation of cyclohexanone oxime wherein the reaction medium comprises a solution containing phosphoric acid, are as follows:

1. formation of hydroxylammonium salt in the hydroxylammonium salt synthesis zone:

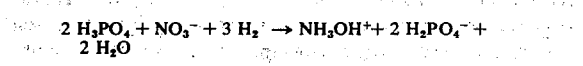

2. formation of cyclohexanone oxime in the oximation zone:

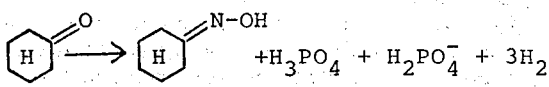

3. make-up, in the form of $HNO_3$, of nitrate ions consumed, after the oxime formed has been separated from the reaction mixture:

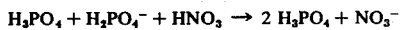

Following the make-up of $HNO_3$, a solution is again available which, after removal of both the water formed by the reaction and the water introduced with the nitric acid make-up, will, theoretically, have the same composition as the initial solution used for the formation of hydroxylammonium salt. This solution is then circulated back to the hydroxylamine synthesis zone. The reduction of the nitrate ions in the hydroxylamine synthesis zone is accomplished in the presence of a catalyst; usually a palladium catalyst is used. The palladium is suspended on a carrier material of carbon or aluminum oxide. The carrier material usually has suspended thereon, for instance, 5–20 weight percent of palladium.

Organic substances, such as the ketone which is to be converted into oxime, and the resulting oxime itself, have an adverse effect on the activity of the catalyst if allowed to come into contact with the catalyst. To prevent the catalyst from being thus poisoned, the circulating reaction medium must be purged of the ketone and oxime contaminants prior to its entering into the hydroxylamine synthesis zone. The ketone and oxime content of the reaction medium should preferably be reduced to a value of not more than 0.02 percent by weight before the reaction medium is recirculated to the hydroxylamine synthesis zone.

In the processes disclosed in the prior art, the aqueous, weak acid reaction liquid coming from the cyclohexanone oxime synthesis zone is treated by means of a stripping process in an attempt to reduce the amount of organic compounds present.

Unfortunately, however, commercial operation of this process including purification of the reaction medium coming from the oxime synthesis zone by stripping, continues to be plagued by residues of ketone or oxime in the aqueous reaction medium which are recycled to the hydroxylammonium synthesis zone. The processes are thus still severely hampered by poisoning of the catalyst.

In the stripping process the ketone is distilled off and the oxime is hydrolyzed according to the reaction

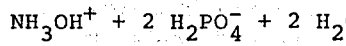

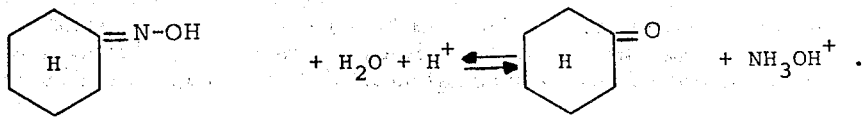

Depending on the temperature, an equilibrium state slowly develops in the liquid being stripped with an equilibrium amount of oxime residue left, which is carried along with the bottom product withdrawn from the stripping column.

It has also been proposed to convert the organic residues into harmless products by heating the circulating reaction medium after the make-up by nitric acid for a time and at such a temperature that the harmful residues are decomposed or oxidized into compounds which are harmless to the activity of the catalyst. The time required to convert the residues to harmless compounds depends in particular on the degree of acidity of the solution and on the temperature; in general, a reaction time of about one hour has been found to be necessary. To maintain the extended reaction time required, the reaction solution circulating from the oxime synthesis zone to the hydroxylamine synthesis zone must be held up in a sizeable reservoir, requiring in addition to the large equipment an equally large volume of reaction solution.

To avoid poisoning the catalyst, the oxime residue must be removed from the circulation liquid or rendered harmless, for instance by an oxidation or decomposition process which converts the oximes to other compounds which do not poison the catalyst.

DETAILED DESCRIPTION OF THE INVENTION

A process has now been found wherein it is possible to shift the hydrolysis-equilibrium between oxime and the corresponding ketone much farther toward formation of the ketone by reacting the hydroxylamine produced by the hydrolysis of the oxime with nitrous gases according to the equation:

$$2 NH_3OH^+ + NO + NO_2 \rightarrow 2 N_2O\uparrow + 3 H_2O + 2H^+.$$

This may be accomplished using two different techniques, as described in more detail below.

THE NITROUS ACID CONTACT-STRIPPING EMBODIMENT

According to one embodiment of the present invention the circulating reaction medium from the oxime synthesis zone which contains oxime and ketone residues dissolved therein is heated to a relatively high temperature of, for instance, 80°C in the presence of nitrous gases. The oxime in the circulating reaction medium is converted by hydrolysis with the nitrous gases into the corresponding ketone during the heat treatment. The ketone produced by the hydrolysis reaction, together with any ketone which was contained in the reaction medium prior to the heat treatment, is removed from the reaction medium by subjecting the reaction medium to a stripping treatment subsequent to the heat treatment. The purified reaction medium can then be recycled to the hydroxylamine synthesis zone without poisoning the palladium catalyst.

This embodiment of the improved process of the present invention is explained in greater detail by reference to FIG. 1 of the accompanying drawings, which figure shows diagrammatically one embodiment of apparatus for performing this process.

Referring to FIG. 1, the hydroxylamine synthesis zone is represented by the letter A and the oxime synthesis zone by the letter B. Hydrogen is fed to the hydroxylamine synthesis zone A through line 1. The hydroxylamine synthesis zone is filled with a palladium catalyst supported on a particulate carrier such as carbon. Any unreacted hydrogen and possible off-gases from the hydroxylamine synthesis are vented through line 2.

The recirculating reaction medium comprising an aqueous solution of a buffer acid such as phosphoric acid or bisulfate, a buffer salt of these acids, or a mixture thereof to which a source of nitrate ions has been added, is introduced to the hydroxylamine synthesis zone A through line 12. The nitrate ions can be added in the form of nitric acid or in the form of nitrous gases wherein nitric acid is formed in the reaction medium in situ. The nitrate ions are catalytically reduced to hydroxylamine by molecular hydrogen. The reaction medium rich in hydroxylamine is withdrawn from hydroxylamine synthesis zone A and fed to the oxime synthesis zone B through line 3.

A ketone, such as cyclohexanone or a ketone dissolved in an organic solvent such as toluene, which is to be reacted with the hydroxylamine in the oxime synthesis zone B, is added to zone B through line 4. The oxime produced by the reaction of the ketone with the hydroxylamine is removed from the oxime synthesis zone B through line 5. If the ketone is fed to the oxime in an organic solvent such as toluene, the organic solvent is removed through line 5 also with the oxime dissolved therein. The aqueous, recirculating reaction medium is withdrawn from the oxime synthesis zone and fed to column F through line 6. The aqueous reaction medium coming from the oxime synthesis zone is impoverished in hydroxylamine, but contains remainders of the ketone and oxime.

Nitrous gases such as a mixture of nitrogen dioxide and nitrogen monoxide are introduced to column F through line 11 and valve 11b and intimately mixed with the aqueous reaction medium. The nitrous gases react with the oxime content of the reaction medium hydrolyzing the oxime back to the ketone. The aqueous reaction medium exiting from the column F through line 16 contains the ketone content which it contained as it came from the oxime synthesis zone as well as the added ketone produced in the column F. The aqueous reaction medium from column F is fed to stripping column C where the ketone is removed overhead as a vapor along with water vapor. The ketone-water vapor overheads are condensed in the form of a water-ketone-azeotrope in condenser D. The condensate passes to separator E wherein the ketone is separated and fed by line 8 back to the oxime synthesis zone B. Part of the water from separator E flows through line 9 to the top of column C and the remainder of the water from separator E being discarded. Condenser D is cooled with cooling water flowing through lines 14 and the stripping column is heated by heating coils 13.

The aqueous circulating reaction medium is withdrawn from the stripping column C and fed to absorber G where nitric acid is formed in situ by absorber G where nitric acid is formed in situ by absorption of nitrous gases supplied to the absorber G through line 11 and valve 11a. The aqueous reaction medium, rich in nitric acid, is then circulated to the hydroxylamine synthesis zone by line 12. Non-absorbed gases exit from the absorber G through line 15.

Instead of absorbing nitrous gases to form nitric acid in situ, a nitric make-up may be added directly to the aqueous recirculating reaction medium whereby the absorption column G can be deleted.

The quantities of nitrous gases to be supplied to column F and absorber G can be controlled by means of the valves 11a and 11b. The total of nitrous gases required could alternatively be fed to column F rather than be split as detailed above. Column F need not be an absorption column, but also can be any reaction vessel in which the aqueous reaction medium is adequately contacted with the nitrous gases.

By way of illustration, the composition of various streams in the process as shown in the drawing and described hereinbefore is given in the following table.

| Process flow | $H_3PO_4$ | $NH_4H_2PO_4$ | $NH_4NO_3$ | $H_2O$ | Oxime | Cyclo-hexanone | $NO+NO_2$ | $N_2$ | $O_2$ | $N_2O$ | C |
|---|---|---|---|---|---|---|---|---|---|---|---|
| 6 | 112 | 88 | 195 | 3238 | 0.50 | — | — | — | — | — | 5.2 |
| 16 | 113.5 | 86.5 | 196.5 | 3232 | — | 0.50 | — | — | — | — | 4.2 |
| 10 | 113.5 | 86.5 | 196.5 | 3224 | — | — | — | — | — | — | 1.2 |
| 12 | 200 | — | 275 | 3000 | — | — | — | — | — | — | 1.0 |
| 11 | — | — | — | — | — | — | 88.5 | 708 | 88.5 | — | — |
| via 11b | | | | | | | 2 | 16 | 2 | — | — |
| 15 | | | | | | | — | 732 | 73.1 | 0.5 | 1.2 |
| 7 | | | | 3 | | 0.50 | | | | | 3.0 |

From the table, it is apparent that the carbon content of the various process streams is larger than would correspond due simply to oxime and ketone contents. This is because in the process some ketone or oxime is always oxidized into organic compounds, such as adipic acid, which have no deterimental effect on the activity of the palladium catalyst at all. Ultimately, these organic compounds are oxidized into water and carbon dioxide. These compounds are also discharged from the cycle with the oxime product.

The various zones in the process can be maintained at atmospheric, sub-atmospheric or at elevated pressures. The temperatures in the hydroxylamine synthesis zone A ranges from about 40°C to about 100°C, that in the oxime synthesis zone B from about 40°C to about 90°C. The stripping column C is operated at temperatures sufficient to remove the ketone-water vapor overhead which in turn depends upon the pressure at which the stripping column is operated. The absorber G is operated at temperatures from about 20°C to about 60°C. The temperature of the column wherein the oxime content of the recirculating, aqueous reaction medium is hydrolyzed to ketone can range between about 40°C to about 100°C.

An essential feature of the present invention is to prevent the noble catalyst from becoming poisoned by oxime and ketone contaminants returning in the recycled, aqueous reaction medium by removing both the oxime and the ketone from the reaction medium prior to its recycling to the hydroxylamine zone.

Instead of reducing nitrate ions in the hydroxylamine zone, nitrogen oxide can be introduced into the hydroxylamine synthesis zone in which a platinum catalyst replaces the palladium catalyst described hereinbefore. The nitrogen oxide is reduced to hydroxylamine in such a process. The platinum catalyst is subject to poisoning just as the palladium catalyst by any oxime or ketone contaminants in the recirculating, aqueous reaction medium. Removing these contaminants by the process as described hereinbefore prevents the poisoning of the platinum catalyst.

The nitrous gases which are added to the aqueous reaction medium during the heat treating step prior to the stripping process can be supplied by adding several varying compounds to the aqueous reaction medium which produce NO and $NO_2$. Nitrous acid itself can be added or nitrous gases such as dinitrogen trioxide can be added which produces nitrous acid on solution in the aqueous reaction medium. Nitrous gases such as nitrogen dioxide and nitric oxide can be added which dissolve readily in the aqueous reaction medium.

The Heating in Contact with Nitrous Acid Embodiment

Another embodiment of my invention is described as follows. I have also found that when nitrous acid is added to the circulating reaction medium from the oxime synthesis zone during the heat treatment, decomposition of the harmful residues, ketones and oximes, can be accomplished at considerably shorter reaction times than for the prior art process described above. For instance, at temperatures of 50°C and higher, a reaction time of only a few minutes will completely decompose the harmful residues to harmless compounds. The nitrous acid can be added in the form of a nitrite solution, preferably an alkali nitrite or by adding nitrous gases.

While nitrous acid need be added only in an amount equal to the substances to be decomposed, an excess of nitrous acid can be used for convenience as it does not harm the activity of the catalyst in the hydroxylammonium salt synthesis zone and is itself converted to hydroxylamine. According to one embodiment of the present invention, nitrous gases are added to the recirculating reaction medium in an amount to supply in whole or in part the nitrate ions necessary in the make-up of the reaction solution fed to the hydroxylammonium salt synthesis zone. The nitrous gases form nitric acid in situ in the recirculating medium. When nitrous gases are used as a source of make-up nitrate, the portion of nitrous gas used to form nitric acid in the reaction medium is added at a relatively low temperature in the range of 20°–40°C. The nitrous gas used as a promoter for the decomposition of the harmful organic residues in the recirculating reaction medium is added to the solution in a reaction zone where the solution is at a higher temperature of 50°C and higher.

This embodiment of the present invention is further described in the following detailed description with reference to the drawing and the following example.

Figure 3:
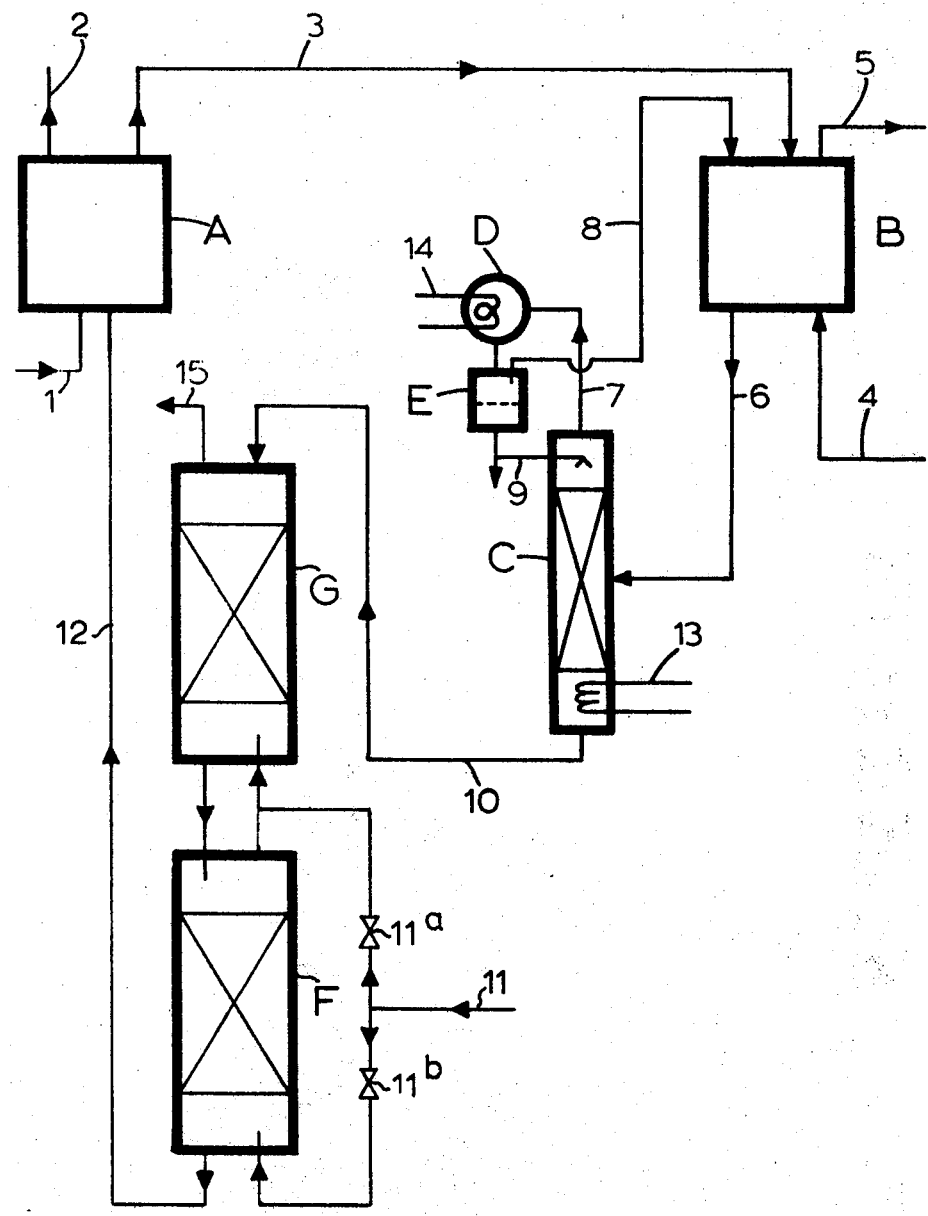
FIG. 3 is a diagrammatic representation of one preferred process of the present invention in which the nitrous acid is added to the circulating reaction medium during the heat treatment step.

One mode of operation of the present invention is shown diagrammatically in FIG. 3 where A and B represent a hydroxylamine synthesis zone and an oxime synthesis zone respectively. Hydrogen is fed to zone A through line 1. The hydroxylamine synthesis zone A is filled with a palladium catalyst supported on a carbon carrier. Unreacted hydrogen and other off-gases are discharged from synthesis zone A through line 2. The recirculating reaction medium containing nitrate ions is introduced to synthesis zone A through line 12.

The hydroxylamine or hydroxylammonium salt enriched solution is withdrawn from synthesis zone A through line 3 and introduced into oxime synthesis zone B. A ketone or a solution of a ketone dissolved in an organic solvent such as toluene is fed to the oxime synthesis zone B through line 4. The oxime produced in the oxime synthesis zone B is withdrawn through line 5. Any solvent introduced with the ketone is also removed through line 5. The hydroxylamine or hydroxylammonium salt impoverished reaction medium is withdrawn from the oxime synthesis zone through line 6. The reaction medium is impoverished in hydroxylamine or hydroxylammonium salt but does contain small amounts of ketone and oxime. This solution is introduced into stripping column C by line 6. In the stripping column C, oxime is hydrolized to ketone. A large part of the ketone thus formed together with the ketone already present, is removed by condenser D where a water-ketone-azeotrope condenses. The condensate flows to separating vessel E, where the water and ketone separate into two phases. The ketone is returned through line 8 to the oxime synthesis zone B. Part of the water flows through line 9 to the top section of column C and the remainder of the water is discarded. Condenser D is cooled with cooling water flowing through cooling coils 14 and the stripping column is supplied heat by heating coils 13.

The reaction medium from stripping column C is fed by line 10 to absorption column G and then to treating reactor F. Nitrous gas is introduced to absorber G through lines 11 and valve 11a and forms nitric acid. Nitrous gas is also introduced into the treating reactor F through line 11 and valve 11b where the nitrous gases accelerate the oxidation and decomposition of the remaining ketone and oxime in the recirculating reaction medium. It is essential that the temperature in the treating reactor F is higher than that in the absorption column G. The temperature in column G ranges between 20° and 40°C and the temperature in treating reactor F being at least 50°C.

The various zones in the process can be maintained at atmospheric, sub-atmospheric or at elevated pressures. The temperature in the hydroxylamine synthesis zone ranges from about 40°C to about 100°C, that in the oxime synthesis zone from about 40°C to about 90°C.

A split nitrous gas feed is shown in FIG. 3 and described above, however, it is also possible for all the nitrous gas to be fed to the treating reactor F and subsequently through absorption column G. Non-absorbed gases are discharged through line 15.

The treating reactor F can be constructed as an absorption column in which the circulating reaction medium and nitrous gases meet in counter-current fashion. However, such a construction is not essential or necessary, any apparatus which provides adequate contact between the gases and the circulation liquid will suffice.

EXAMPLE

The unexpected improvement which accompanies the presence of a small quantity of nitrite ions in the reaction medium during a heat treatment to decompose ketone and oxime contaminants in the reaction medium is shown in the following comparative examples.

A solution exiting from the stripping column of a process as shown in FIG. 3 was found to be composed of $H_3PO_4$, $NH_4NO_3$ and $H_2O$ having the molar proportions of 2 parts $H_3PO_4$, 2.75 parts $NH_4NO_3$ and 30 parts $h_2O$. The solution also contained 0.05 percent by weight of cyclohexanone oxime.

Figure 1:
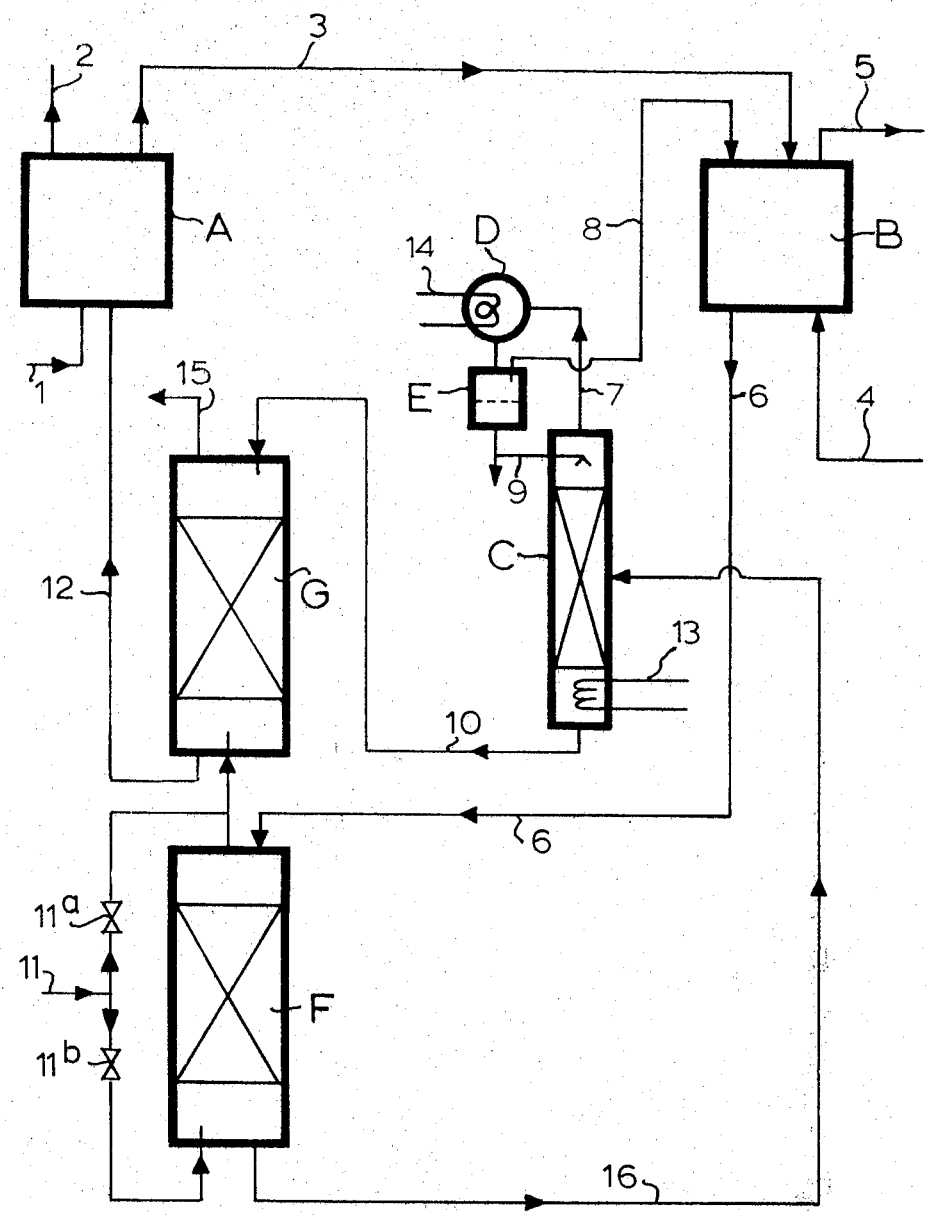
Figure 2:
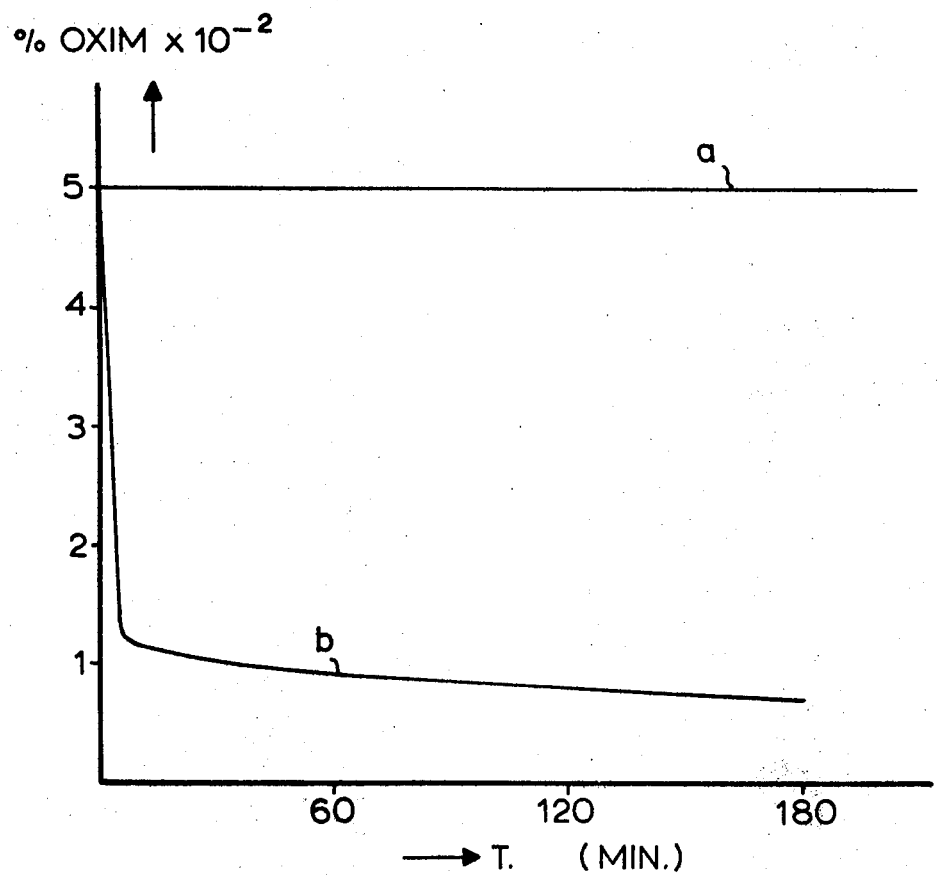
FIG. 2 is a graph showing the percent oxime in the recirculating reaction medium after various times of being heated to 50°C. The line denoted by the letter $a$ represents the recirculating solution from the oxime synthesis zone which was not heated in the presence of nitrous acid and the line denoted by the letter $b$ represents the same solution which was heated in the presence of nitrous acid.

A portion of this solution was heated to a temperature of 50°C and the concentration of oxime measured at various time intervals. The results of these measurements are plotted as line a in FIG. 2. As can be seen, the concentration of the oxime remained essentially unchanged.

A second portion of the above-mentioned solution from the stripping column containing approximately 200 moles $H_3PO_4$, 275 moles $NH_4NO_3$, 3000 moles $H_2O$ and 0.05% by weight of oxime was heated to 50°C in the presence of 45 millimoles of $NO_2^-$ per kilogram and the oxime concentration measured at various time intervals. The results are shown as line b of FIG. 2. As can be seen, the oxime concentration fell rapidly within the first few minutes to approximately 0.01 percent by weight.

The nitrous acid component which is added to the aqueous reaction medium during the heat treating step can be supplied by adding several varying compounds to the aqueous reaction medium which produce nitrite ($NO_2^-$) ions. Nitrous acid itself can be added or nitrous gases such as dinitrogen trioxide can be added which produces nitrous acid on solution in the aqueous reaction medium. Nitrous gases such as nitrogen dioxide can be added which dissolve readily in the aqueous reaction medium forming a mixture of nitrate ions and nitrite ions.

What is claimed is:

1. In a cyclic process for producing cyclohexanone oxime wherein a buffered, aqueous reaction medium containing a member selected from the group consisting of phosphoric acid, ammonium bisulfate, buffer salts of said phosphoric acid and said bisulfate and mixtures thereof is circulated between a hydroxylamine synthesis zone and a cyclohexanone oxime synthesis zone, a source of a nitrogen containing member selected from the group consisting of nitrate ions and nitrogen oxide being supplied to said reaction medium as said reaction medium circulates from said oxime synthesis zone to said hydroxylamine synthesis zone, said hydroxylamine synthesis zone containing a noble metal catalyst, introducing molecular hydrogen to said hydroxylamine synthesis zone, said nitrogen containing member being catalytically reduced by said hydrogen to hydroxylamine in said hydroxylamine synthesis zone, withdrawing said reaction medium being rich in hydroxylamine from the hydroxylamine synthesis zone and circulating said hydroxylamine rich, reaction medium to said oxime synthesis zone, said oxime synthesis zone being supplied with cyclohexanone, said cyclohexanone being converted to cyclohexanone oxime by reacting with said hydroxylamine in said oxime synthesis zone, separating said cyclohexanone from said aqueous reaction medium and recycling said aqueous reaction medium to said hydroxylamine synthesis zone, the improvement consisting of subjecting said recirculating, aqueous reaction medium from said oxime synthesis zone, first to contact with a nitrous gas at a temperature of at least 40°C to hydrolyze any residue cyclohexanone oxime in said aqueous recirculating medium to cyclohexanone and second to a stripping step wherein residue cyclohexanone is removed from said recirculating, aqueous reaction medium.

2. In a process for producing cyclohexanone oxime in which a buffered, acidic reaction medium comprising an aqueous solution containing a member selected from the group consisting of phosphoric acid, ammonium bisulfate, buffer salts of said phosphoric acid and said bisulfate is cycled from a hydroxylamine synthesis zone to a cyclohexanone oxime synthesis zone, and back to the hydroxylamine synthesis zone, wherein nitrate ions are obtained in said solution by addition of nitric acid to said solution just prior to introduction into the hydroxylamine synthesis zone and molecular hydrogen is added to the hydroxylamine synthesis zone, heating the circulating reaction medium as it recirculates between the oxime synthesis zone and the hydroxylamine synthesis zone, said nitrate ions being catalytically reduced to hydroxylamine with said molecular hydrogen in the presence of a supported palladium metal catalyst contained in the hydroxylamine synthesis zone, the solution rich in hydroxylamine from the hydroxylamine synthesis zone is fed with cyclohexanone to said cyclohexanone oxime synthesis zone wherein the hydroxylamine and the cyclohexanone react with each other to form cyclohexanone oxime, separating the cyclohexanone oxime and unreacted cyclohexanone from said solution and recycling said solution back to said hydroxylamine synthesis zone, the improvement consisting essentially of reducing said heating time by supplying at least part of the nitrate ions by absorption of nitrous gases in the recirculating acid reaction medium at a temperature of 20°–40°C, followed by contacting the recirculating acid reaction medium with nitrous gases at a temperature of at least 50°C.

* * * * *

UNITED STATES PATENT OFFICE
CERTIFICATE OF CORRECTION

Patent No. 3,948,988     Dated  April 6, 1976

Inventor(s)  Abraham H. De Rooij

It is certified that error appears in the above-identified patent and that said Letters Patent are hereby corrected as shown below:

In the heading:

Insert priority data as follows:

--Netherlands Application No. 7001905
        filed February 11, 1970
      Netherlands Application No. 7001906
        filed February 11, 1970--

Signed and Sealed this

Twenty-sixth Day of October 1976

[SEAL]

Attest:

RUTH C. MASON
*Attesting Officer*

C. MARSHALL DANN
*Commissioner of Patents and Trademarks*